United States Patent
Salamone et al.

(10) Patent No.: US 6,908,978 B2
(45) Date of Patent: Jun. 21, 2005

(54) HIGH REFRACTIVE INDEX POLYMERIC SILOXYSILANE COMPOSITIONS

(75) Inventors: Joseph C. Salamone, Boca Raton, FL (US); Jay F. Kunzler, Canadaigua, NY (US); Richard M. Ozark, Solvay, NY (US); David E. Seelye, North Chili, NY (US)

(73) Assignee: Bausch & Lomb Incorporated, Rochester, NY (US)

( * ) Notice: Subject to any disclaimer, the term of this patent is extended or adjusted under 35 U.S.C. 154(b) by 0 days.

(21) Appl. No.: 10/000,136

(22) Filed: Nov. 2, 2001

(65) Prior Publication Data

US 2003/0100697 A1 May 29, 2003

(51) Int. Cl.[7] .............................................. C08G 77/04
(52) U.S. Cl. ...................... 528/43; 556/437; 556/458; 556/445; 528/32; 528/31; 526/279; 525/288; 568/673
(58) Field of Search .................. 556/437, 458, 556/445; 528/32, 31, 43; 526/279; 525/288; 568/673

(56) References Cited

U.S. PATENT DOCUMENTS

| | | |
|---|---|---|
| 3,996,187 A | 12/1976 | Travnicek ..................... 260/37 |
| 3,996,189 A | 12/1976 | Travnicek ..................... 260/37 |
| 4,418,165 A | 11/1983 | Polmanteer et al. ........ 523/210 |
| 4,647,282 A | 3/1987 | Fedorov et al. ................. 623/4 |
| 4,690,993 A | 9/1987 | Falcetta et al. ............. 526/242 |
| 4,868,251 A | 9/1989 | Reich et al. ................. 525/479 |
| 4,954,586 A * | 9/1990 | Toyoshima et al. |
| 5,336,797 A * | 8/1994 | McGee et al. ............... 556/419 |
| 5,512,609 A | 4/1996 | Yang .......................... 523/107 |
| 5,623,029 A | 4/1997 | Yang .......................... 525/478 |
| 5,770,669 A | 6/1998 | Robertson et al. .......... 526/279 |
| 2002/0075448 A1 | 6/2002 | Kunzler et al. ............. 351/160 |

FOREIGN PATENT DOCUMENTS

| | | |
|---|---|---|
| EP | 0 231 572 | 8/1987 |
| EP | 0 396 364 | 7/1990 |
| EP | 0 918 233 A2 | 5/1999 |
| JP | 62 296118 A | 12/1987 |
| JP | 09 221530 A | 8/1997 |
| JP | 2001 048939 A | 2/2001 |
| JP | 2001 172391 A | 6/2001 |
| JP | 2001 323024 A | 11/2001 |
| JP | 2001 323026 A | 11/2001 |
| WO | WO 01/70824 A2 | 9/2001 |

* cited by examiner

*Primary Examiner*—Kuo-Liang Peng
(74) *Attorney, Agent, or Firm*—Rita D. Vacca; Toan P. Vo

(57) ABSTRACT

Optically transparent, relatively high refractive index polymeric compositions and ophthalmic devices such as intraocular lenses, contact lenses and corneal inlays made therefrom are described herein. The preferred polymeric compositions are produced through the polymerization of one or more siloxysilane monomers or the copolymerization of one or more siloxysilane monomers with one or more aromatic or non-aromatic non-siloxy monomers, hydrophobic monomers or hydrophilic monomers.

17 Claims, 1 Drawing Sheet

HIGH REFRACTIVE INDEX POLYMERIC SILOXYSILANE COMPOSITIONS

FIELD OF THE INVENTION

Figure 1:
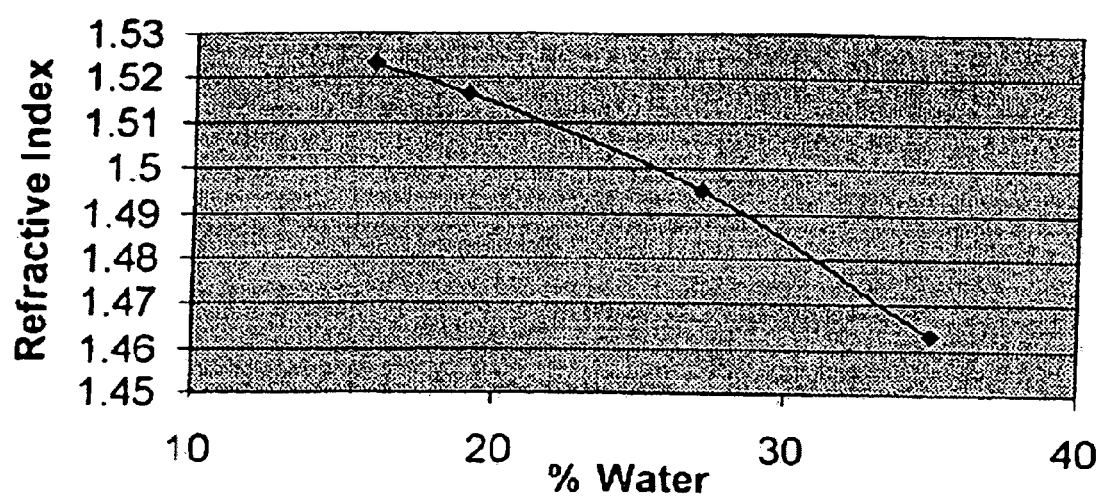

The present invention relates to monomers useful in the manufacture of biocompatible medical devices. More particularly, the present invention relates to siloxysilane monomers capable of polymerization or copolymerization to form polymeric compositions having desirable physical characteristics for use in the manufacture of ophthalmic devices.

BACKGROUND OF THE INVENTION

Since the 1940's ophthalmic devices in the form of intraocular lens (IOL) implants have been utilized as replacements for diseased or damaged natural ocular lenses. In most cases, an IOL is implanted within an eye at the time of surgically removing the diseased or damaged natural lens, such as for example, in the case of cataracts. For decades, the preferred material for fabricating such IOL implants was poly(methyl methacrylate) (PMMA), which is a rigid, glassy polymer.

Softer, more flexible IOL implants have gained in popularity in more recent years due to their ability to be compressed, folded, rolled or otherwise deformed. Such softer IOL implants may be deformed prior to insertion thereof through an incision in the cornea of an eye. Following insertion of the IOL in an eye, the IOL returns to its original pre-deformed shape due to the memory characteristics of the soft material. Softer, more flexible IOL implants as just described may be implanted into an eye through an incision that is much smaller, i.e., less than 4.0 mm, than that necessary for more rigid IOLs, i.e., 5.5 to 7.0 mm. A larger incision is necessary for more rigid IOL implants because the lens must be inserted through an incision in the cornea slightly larger than the diameter of the inflexible IOL optic portion. Accordingly, more rigid IOL implants have become less popular in the market since larger incisions have been found to be associated with an increased incidence of postoperative complications, such as induced astigmatism.

With recent advances in small-incision cataract surgery, increased emphasis has been placed on developing soft, foldable materials suitable for use in the manufacture of IOL implants. In general, the materials of current commercial IOLs fall into one of three categories: silicone, hydrophilic acrylic and hydrophobic acrylic.

In general, high water content, i.e., 15 percent or greater water content by volume, hydrophilic acrylic materials or "hydrogels," have relatively low refractive indexes, making them less desirable than other materials with respect to minimal incision size. Low refractive index materials require a thicker IOL optic portion to achieve a given refractive power. Silicone materials may have a higher refractive index than high-water content hydrogels, but tend to unfold explosively after being placed in the eye in a folded position. Explosive unfolding can potentially damage the corneal endothelium and/or rupture the natural lens capsule and associated zonules. Low glass transition temperature hydrophobic acrylic materials are desirable because they typically have a high refractive index and unfold more slowly and more controllably than silicone materials. Unfortunately, low glass transition temperature hydrophobic acrylic materials, which contain little or no water initially, may absorb pockets of water in vivo causing light reflections or "glistenings." Furthermore, it may be difficult to achieve ideal folding and unfolding characteristics due to the temperature sensitivity of some hydrophobic acrylic polymers.

Because of the noted shortcomings of current polymeric materials available for use in the manufacture of ophthalmic devices such as IOLs, there is a need for stable, biocompatible polymeric materials having desirable physical characteristics.

SUMMARY OF THE INVENTION

Soft, foldable, relatively high refractive index, polymeric compositions of the present invention are synthesized through the polymerization of one or more siloxysilane monomers or alternatively through the copolymerization of one or more siloxysilane monomers with one or more aromatic or non-aromatic non-siloxy based monomers, hydrophilic monomers or hydrophobic monomers. Polymeric compositions of the present invention are gas permeable, transparent, relatively high in strength for durability during surgical manipulation and relatively high in refractive index. The subject polymeric compositions are particularly well suited for use in the manufacture of ophthalmic devices such as but not limited to intraocular lens (IOL) implants, contact lenses, keratoprostheses, corneal rings, corneal inlays and the like.

Preferred siloxysilane monomers for use in preparing the polymeric compositions of present invention are represented by the structures of Formula 1 and Formula 2 below:

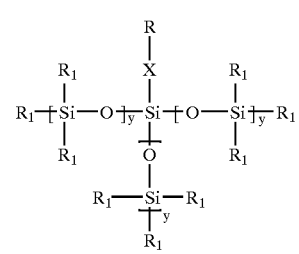

Formula 1

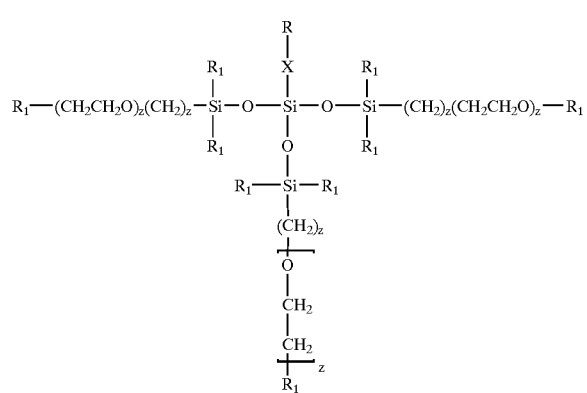

Formula 2 wherein R is a polymerizable group; X is selected from the group consisting of $C_{1-10}$ alkyl, $C_{1-10}$ alkyloxy, $C_{6-36}$ aryl and $C_{6-36}$ aryloxy; and the $R_1$ groups may be the same or different selected from the group consisting of $C_{1-10}$ alkyl, $C_{1-20}$ cycloalkyl, $C_{6-36}$ aryl, $C_{6-36}$ aryl ether, $C_{6-36}$ heterocycle, $C_{6-36}$ heterocycle with on or more substituents, $C_{1-10}$ alkyl ether and $C_{6-36}$ aryloxy; y may be the same or different non-negative integer less than 101; and z may be the same or different non-negative integer less than 20.

Accordingly, it is an object of the present invention to provide a transparent, biocompatible polymeric composition having desirable physical characteristics for use in the manufacture of ophthalmic devices.

Another object of the present invention is to provide a polymeric composition having a relatively high refractive index.

Another object of the present invention is to provide a polymeric composition suitable for use in the manufacture of an ophthalmic implant.

Another object of the present invention is to provide a polymeric composition that is relatively flexible with good clarity.

Still another object of the present invention is to provide a polymeric composition that is relatively simple to produce.

These and other objectives and advantages of the present invention, some of which are specifically described and others that are not, will become apparent from the detailed description and claims that follow.

DETAILED DESCRIPTION OF THE INVENTION

The present invention relates to siloxysilane monomers and the use of such monomers to produce biocompatible polymeric compositions having desirable physical properties for use in the manufacture of ophthalmic devices. The siloxysilane monomers of the present invention are represented generally by Formula 1 and Formula 2 below,

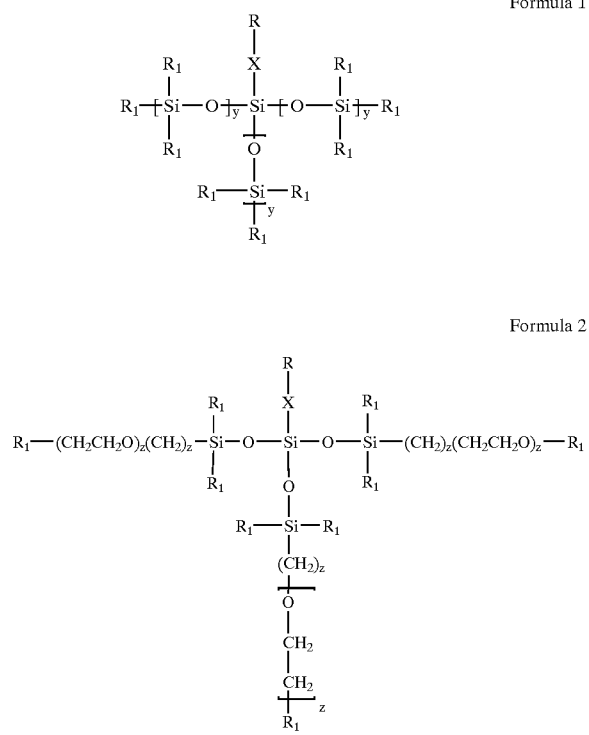

Formula 1

Formula 2 wherein R is a polymerizable group selected from the group consisting of methacrylate, acrylate, acrylamido, methacrylamido, styryl, itaconate, fumaroyl, vinyl, vinyloxy, vinyl carbamate and vinyl carbonate; X is selected from the group consisting of $C_{1-10}$ alkyl such as for example but not limited to methyl, propyl or heptyl, $C_{1-10}$ alkyloxy such as for example but not limited to ethyloxy, butyloxy or octyloxy, $C_{6-36}$ aryl such as for example but not limited to phenyl or naphthyl and $C_{6-36}$ aryloxy such as for example but not limited to phenyloxy or naphthyloxy; the $R_1$ groups may be the same or different selected from the group consisting of $C_{1-10}$ alkyl such as for example but not limited to methyl, propyl or pentyl but preferably propyl for increased stability, $C_{1-20}$ cycloalkyl such as for example but not limited to cyclohexyl or cycloheptyl, $C_{6-36}$ aryl such as for example but not limited to phenyl or naphthyl, $C_{6-36}$ aryl ether such as for example but not limited to phenyl ether or naphthyl ether, $C_{6-36}$ heterocycle such as for example but not limited to pyridine, quinoline, furan or thiophene but preferably pyridine to increase refractive index, $C_{6-36}$ heterocycle such as those described above with one or more substituents such as for example but not limited to chlorine, fluorine, amine, amide, ketone or $C_{1-3}$ alkyl such as for example methyl or propyl, $C_{6-36}$ aryloxy such as for example but not limited to phenyloxy or naphthyloxy and $C_{1-10}$ alkyl ethers such as for example methyl ether or propyl ether; y may be the same or different non-negative integer less than 101; and z may be the same or different non-negative integer less than 20.

Siloxysilane monomers of the present invention represented by Formula 1 and Formula 2 above, may be synthesized through a co-hydrolysis reaction with an acid scavenger as illustrated in Scheme 1 below.

Scheme 1

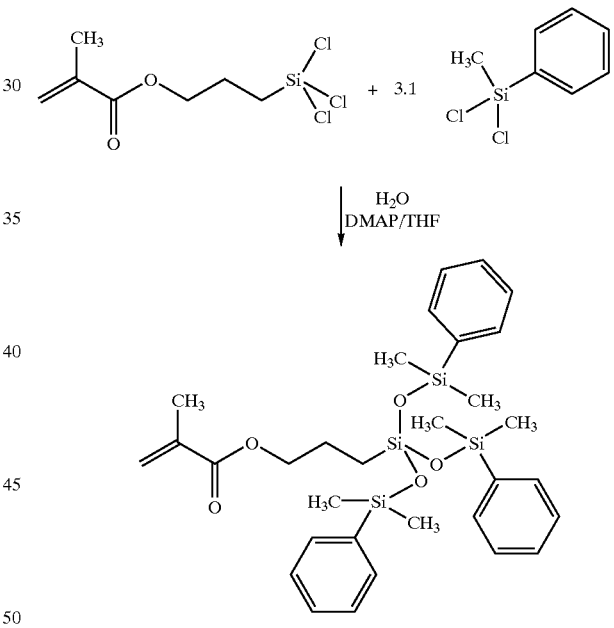

As illustrated in Scheme co-hydrolysis of 1,3-methacryloyloxypropylchlorosilane with chlorophenyldimethylsilane using N,N-dimethylaminopyridine (DMAP) as an acid scavenger produces 3-methacryloyloxypropyltris (phenyldimethylsiloxy)silane.

Examples not intended to be limiting of siloxysilane monomers of the present invention produced as described above include for example but are not limited to m-vinylbenzyltris(trimethylsiloxy)silane, p-vinylbenzyltris(trimethylsiloxy)silane, m-vinylbenzyltris(dimethylphenylsiloxy)silane, p-vinylbenzyltris(dimethylphenylsiloxy)silane, 3-methacryloyloxy-propyltris(triphenylsiloxy)silane, 3-(triphenylsilyl)propyl vinyl ether, 3,3-diphenyl propyl maleimide, 2-bromobenzyl-4-ethenylphenylether, (3-phenyldimethylsilylpropyl)-4-ethenylphenylether and 3-acryloyloxypropyl-1,1-diphenyl-(2-naphthyl)silane.

Although one or more siloxysilane monomers of the present invention may be polymerized or copolymerized to form crosslinked three-dimensional networks, one or more crosslinking agents may be added thereto in quantities less than 10 percent weight per volume (W/V) if desired prior to polymerization or copolymerization thereof.

Examples of suitable crosslinking agents include but are not limited to diacrylates and dimethacrylates of triethylene glycol, butylene glycol, neopentyl glycol, ethylene glycol, hexane-1,6-diol and thio-diethylene glycol, trimethylolpropane triacrylate, N,N'-dihydroxyethylene bisacrylamide, diallyl phthalate, triallyl cyanurate, divinylbenzene; ethylene glycol divinyl ether, N,N'-methylene-bis-(meth)acrylamide, sulfonated divinylbenzene and divinylsulfone.

Although not required, siloxysilane monomers within the scope of the present invention may optionally have one or more strengthening agents added thereto prior to polymerization or copolymerization, preferably in quantities of less than about 80 weight percent but more typically from about 20 to about 60 weight percent.

Examples of suitable strengthening agents are described in U.S. Pat. Nos. 4,327,203, 4,355,147 and 5,270,418 each incorporated herein in its entirety by reference. Specific examples, not intended to be limiting, of such strengthening agents include cycloalkyl acrylates and methacrylates, such as for example tert-butylcyclohexyl methacrylate, isopropylcyclopentyl acrylate and tert-butylcyclohexyl acrylate.

One or more ultraviolet light absorbers may optionally be added to the subject monomers prior to polymerization or copolymerization in quantities typically less than 2 percent W/V. Suitable ultraviolet light absorbers for use in the present invention include for example but are not limited to β-(4-benzotriazoyl-3-hydroxyphenoxy)ethyl acrylate, 4-(2-acryloyloxyethoxy)-2-hydroxybenzophenone, 4-methacryloyloxy-2-hydroxybenzophenone, 2-(2'-methacryloyloxy-5'-methylphenyl)benzotriazole, 2-(2'-hydroxy-5'-methacryloyloxyethylphenyl)-2H-benzotriazole, 2-[3'-tert-butyl-2'-hydroxy-5'-(3"-methacryloyloxypropyl)phenyl]-5-chlorobenzotriazole, 2-[3'-tert-butyl-5'-(3"-dimethylvinylsilylpropoxy)-2'-hydroxyphenyl]-5-methoxybenzotriazole, 2-(3'-allyl-2'-hydroxy-5'-methylphenyl)benzotriazole, 2-[3'-tert-butyl-2'-hydroxy-5'-(3"-methacryloyloxypropoxy)phenyl]-5-methoxybenzotriazole, and 2-[3'-tert-butyl-2'-hydroxy-5'-(3"-methacyloyloxypropoxy)phenyl]-5-chlorobenzotriazole wherein β-(4-benzotriazoyl-3-hydroxyphenoxy)ethyl acrylate is the preferred ultraviolet light absorber.

The siloxysilane monomers of the present invention produced as described above may be polymerized alone or copolymerized with other monomers. The subject siloxysilane monomers may be copolymerized with one or more aromatic or non-aromatic non-siloxy-based monomers, hydrophobic monomers, hydrophilic monomers or a combination thereof to produce polymeric compositions of the present invention.

Examples of aromatic and non-aromatic non-siloxy-based monomers useful for copolymerization with one or more siloxysilane monomers of the present invention include for example but are not limited to 2-phenyloxyethyl methacrylate, 3,3-diphenylpropyl methacrylate, glyceryl methacrylate, 3-phenylpropyl acrylate, N,N-dimethylacrylamide, methyl methacrylate, 2-(1-naphthylethyl methacrylate) and 2-(2-naphthylethyl methacrylate) but preferably 2-(1-naphthylethyl methacrylate) for increased refractive index.

Examples of hydrophobic monomers useful for copolymerization with one or more siloxysilane monomers of the present invention include for example but are not limited to 2-ethylhexyl methacrylate, 3-methacryloyloxypropyldiphenylmethylsilane and 2-phenyloxyethyl methacrylate but preferably 3-methacryloyloxypropyldiphenylmethylsilane for increased refractive index.

Examples of hydrophilic monomers useful for copolymerization with one or more siloxysilane monomers of the present invention include for example but are not limited to N,N-dimethylacrylamide and N-methylacrylamide but preferably N,N-dimethylacrylamide for increased hydrophilicity.

The physical and mechanical properties of copolymers produced from siloxysilane monomers of the present invention are set forth below in

BRIEF DESCRIPTION OF THE INVENTION

FIG. 1 Dependance of water content versus refractive index for copolymers based on MPTDS and DMA.

FIG. 1 Dependence of water content versus refractive index for copolymers based on MPTDS and DMA. Table 1 and FIG. 1.

TABLE 1

Mechanical and physical property results for films based on 3-(3-methacryloyloxypropyl)-1,1,1-triphenyl-3,3-dimethyldisiloxane (MPTDS) or the acrylate (APTDS).

| Composition | W/W % | R.I. | Mod (g/mm$^2$) | Tear (g/mm) | % H$_2$O |
|---|---|---|---|---|---|
| MPTDS/Dar | 100/0.5 | 1.54 | | | 0 |
| MPTDS/DMA/Eg/Dar/Hex | 54/40/3.2/2.2/20 | 1.49 | 1703 | 35 | 28 |
| | 56/42/.4/1.5/20 | 1.46 | 337 | 54 | 43 |
| | 64/33/2/1/20 | 1.51 | 4333 | 112 | 23 |

TABLE 1-continued

Mechanical and physical property results for films based on 3-(3-methacryloyloxypropyl)-1,1,1-triphenyl-3,3-dimethyldisiloxane (MPTDS) or the acrylate (APTDS).

| Composition | W/W % | R.I. | Mod (g/mm$^2$) | Tear (g/mm) | % H$_2$O |
|---|---|---|---|---|---|
| APTDS/Dar | 100/0.5 | 1.54 | | | 0 |
| APTDS/DMA/Eg/Dar/Hex | 70/30/1/0.5/20 | 1.524 | 251 | 64 | 17 |
| | 60/40/1/0.5/20 | 1.49 | 78 | 24 | 30 |
| APTDS/DMA/Hex/Eg/Irg | 65/35/20/1/0.5 | 1.52 | 121 | 37 | 19 |

R.I. = Refractive Index
Mod = Modulus
Eg = Egdma = Ethylene glycol dimethacrylate
DMA = Dimethylacrylamide
Hex = Hexanol
Dar = Darocur ™ 1173 (EM Industries)
Irg = Irgacure ™ 819 (Ciba-Geigy, Basel, Switzerland)

No water content, low water content of less than 15 percent water content by volume and high water content "hydrogels" of 15 percent or higher water content by volume polymeric compositions of the present invention having ideal physical characteristics for ophthalmic device manufacture are described herein.

The polymeric compositions of the present invention are of relatively high refractive index of approximately 1.45 or greater and relatively high elongation of approximately 100 percent or greater. The polymeric compositions of the present invention with the desirable physical properties noted above are particularly useful in the manufacture of ophthalmic devices such as but not limited to relatively thin, foldable intraocular lens implants, contact lenses and corneal inlays.

IOLs having relatively thin optic portions are critical in enabling a surgeon to minimize surgical incision size. Keeping the surgical incision size to a minimum reduces intraoperative trauma and postoperative complications. A relatively thin IOL optic portion is also critical for accommodating certain anatomical locations in the eye such as the anterior chamber and the ciliary sulcus. IOLs may be placed in the anterior chamber for increasing visual acuity in either aphakic or phakic eyes, or placed in the ciliary sulcus for increasing visual acuity in phakic eyes.

The polymeric compositions of the present invention have the flexibility required to allow implants manufactured from the same to be folded or deformed for insertion into an eye through the smallest possible surgical incision, i.e., 3.5 mm or smaller. It is unexpected that the subject polymeric compositions could possess the ideal physical properties described herein. The ideal physical properties of the subject polymeric compositions are unexpected since high refractive index monomers typically lend to polymers with increased crystallinity and decreased clarity, which is not true in the case of the subject polymeric compositions.

The subject siloxysilane monomers and polymeric compositions produced therefrom are described in still greater detail in the examples that follow.

EXAMPLE 1

Synthesis of MPTDS

To a 1000 ml one-neck round bottom flask fitted with a magnetic stirrer, condenser, heating mantle and nitrogen blanket, was added 500 ml CHCl$_3$, 18.2 grams (149 mmol) of dimethylaminopyridine (DMAP), 37.6 grams (135.9 mmol) of triphenylsilanol and 30.0 grams (135.9 mmol) of 3-methacryloyloxypropyldimethylchlorosilane. The contents of the flask were refluxed for 72 hours and then allowed to cool to room temperature. The organics were washed twice in 500 ml 2N HCl, then dried over magnesium sulfate and flashed to an oil. After column chromatography on silica gel eluting with 80.0% heptane and 20.0% CH$_2$Cl$_2$, the product was isolated. The chromatography was monitored by thin layer chromatography (TLC) plates.

EXAMPLE 2

To 64 parts of MPTDS was added 33 parts of dimethylacrylamide, 20 parts of hexanol, 2 parts of ethyleneglycol dimethacrylate and 1.0% of Irgacure™ 819 as the UV photoinitiator and 0.25% of a commercial triazole UV blocker (Aldrich Chemical Co). The clear solution was sandwiched between two silanized glass plates using metal gaskets and exposed to UV radiation for two hours. The resultant films were released and extracted in isopropanol (IPA) for four hours, followed by air-drying and a 30 mm vacuum to remove the IPA. The resultant film was hydrated at room temperature overnight in borate buffered saline. The clear tack-free films possessed a modulus of 4333 g/mm$^2$, a tear strength of 112 g/mm, a water content of 23% and a refractive index of 1.51.

EXAMPLE 3

To 70 parts of APTDS was added 30 parts of dimethylacrylamide, 20 parts of hexanol, 1 part of ethyleneglycol dimethacrylate and 0.5% of Irgacure™ 819 as the UV photoinitiator and 0.25% of a commercial triazole UV blocker (Aldrich Chem. Co). The clear solution was sandwiched between two silanized glass plates using metal gaskets and exposed to UV radiation for two hours. The resultant films were released and extracted in IPA for four hours, followed by air-drying and a 30 mm vacuum to remove the IPA. The resultant film was hydrated at room temperature overnight in borate buffered saline. The clear tack-free films possessed a modulus of 251 g/mm$^2$, a tear strength of 64 g/mm, a water content of 17% and a refractive index of 1.52.

EXAMPLE 4

To 70 parts of APTDS was added 10 parts of dimethylacrylamide, 20 parts of hexanol, 1 part of ethyleneglycol dimethacrylate and 0.5% of Irgacure™ 819 as the UV photoinitiator and 0.25% of a commercial triazole UV blocker (Aldrich Chem. Co). The clear solution was sandwiched between two silanized glass plates using metal gaskets and exposed to UV radiation for two hours. The resultant films were released and extracted in IPA for four hours, followed by air-drying and a 30 mm vacuum to remove the IPA. The resultant film was hydrated at room temperature overnight in borate buffered saline. The clear tack-free films possessed a water content of 10% and a refractive index of 1.53.

The siloxysilane monomers of the present invention may be readily cured in cast shapes by one or more conventional methods. Such methods include for example but are not limited to ultraviolet light (UV) polymerization, visible light polymerization, microwave polymerization, thermal polymerization, free radical polymerization, living radical polymerization or combinations thereof. Metallocene catalysts may also be used in certain instances.

One or more suitable free radical thermal polymerization initiators may be added to the monomers of the present invention. Examples of such initiators include but are not limited to organic peroxides, such as acetyl peroxide, lauroyl peroxide, decanoyl peroxide, stearoyl peroxide, benzoyl peroxide, tert-butyl peroxypivalate, peroxydicarbonate, and the like. Preferably such an initiator is employed in a concentration of approximately 0.01 to 1 percent by weight of the total monomer mixture.

Representative UV initiators include those known in the field such as for example but not limited to benzoin methyl ether, benzoin ethyl ether, Darocur™ 1173, 1164, 2273, 1116, 2959, 3331 (EM Industries) and Irgacur™ 651 and 184 (Ciba-Geigy, Basel, Switzerland).

Ophthalmic devices such as but not limited to IOLs made of the polymeric compositions of the present invention can be of any suitable design or form. For example, ophthalmic devices such as IOLs typically comprise an optic portion and one or more haptic portions. Once implanted within an eye, the IOL optic portion reflects light onto the retina of the eye and the permanently attached haptic portions hold the optic portion in proper alignment within the eye. The haptic portions may be integrally formed with the optic portion in a one-piece design or attached by staking, adhesives or other methods known to those skilled in the art in a multipiece design.

The subject ophthalmic devices, such as for example IOLs, may be manufactured to have an optic portion and haptic portions made of the same or differing materials. Preferably, in accordance with the present invention, both the optic portion and the haptic portions of the IOL are made of the same polymeric composition of the present invention. Alternatively however, the IOL optic portion and haptic portions may be manufactured from different materials and/or different formulations of the polymeric compositions of the present invention, such as described in detail in U.S. Pat. Nos. 5,217,491 and 5,326,506, each incorporated herein in its entirety by reference. Once the particular material or materials are selected, the same is either cast in molds of the desired form and cured, or cast in the form of rods and cured. If cast in the form of rods, the rods while in a dry state are machined or lathed into disks. The resultant disks may then be machined or lathed into IOLs or other ophthalmic devices. The IOLs or other ophthalmic devices whether molded or machined/lathed are then cleaned, polished, hydrated, packaged and sterilized by customary methods known to those skilled in the art.

In addition to IOLs, the polymeric compositions of the present invention are also suitable for use as other ophthalmic devices such as but not limited to contact lenses, keratoprostheses, capsular bag extension rings, corneal inlays, corneal rings and like devices.

IOLs and like ophthalmic devices manufactured using the unique polymeric compositions produced from the unique siloxysilane monomers of the present invention are used as customary in the field of ophthalmology. For example, in a surgical procedure, an incision is placed in the cornea of an eye. Most commonly through the corneal incision the natural lens of the eye is removed (aphakic application) such as in the case of a cataractous natural lens. An IOL or the like is then inserted into the anterior chamber, posterior chamber or lens capsule of the eye prior to closing the incision. However, the ophthalmic devices of the subject invention may be used in accordance with other surgical procedures known to those skilled in the field of ophthalmology.

While there is shown and described herein certain siloxysilane monomers and polymeric compositions of the present invention, it will be manifest to those skilled in the art that various modifications may be made without departing from the spirit and scope of the underlying inventive concept and that the same is not limited to particular structures herein shown and described except insofar as indicated by the scope of the appended claims.

We claim:

1. A polymeric composition produced through the polymerization of one or more siloxysilane monomers comprising:

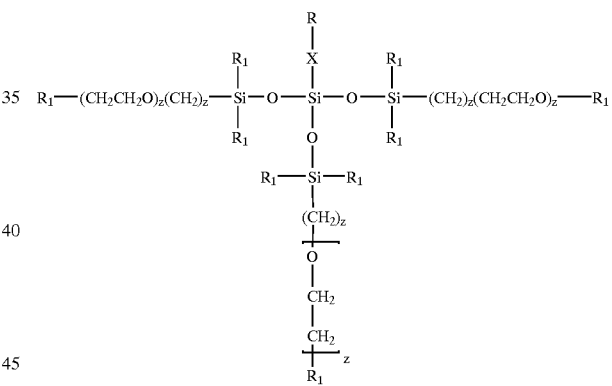

wherein R is a polymerizable group: X is selected from the group consisting of $C_{1-10}$ {alkyl} alkylene, $C_{1-10}$ {alkyloxy} alkyleneoxy, $C_{6-36}$ {aryl} arylene and $C_{6-36}$ {aryloxy} aryleneoxy; {and} the $R_1$ groups may be the same or different selected from the group consisting of $C_{1-10}$ alkyl, $C_{1-20}$ cycloalkyl, $C_{6-36}$ aryl, $C_{6-36}$ aryl ether, $C_{6-36}$ heterocycle, $C_{6-36}$ heterocycle with one or more substituents, $C_{1-10}$ alkyl ether and $C_{6-36}$ aryloxy; and z may be the same or different and is an integer greater than or equal to 1, but less than 20.

2. A polymeric composition produced through the copolymerization of one or more monomers of claim 1 with one or more aromatic or non-aromatic non-siloxy-based monomers.

3. A polymeric composition produced through the copolymerization of one or more monomers of claim 1 with one or more hydrophobic monomers.

4. A polymeric composition produced through the copolymerization of one or more monomers of claim 1 with one or more hydrophilic monomers.

5. The polymeric composition of claim 2 wherein said one or more aromatic or non-aromatic non-siloxy-based monomers are selected from the group consisting of 2-phenyloxyethyl methacrylate, 3,3-diphenylpropyl methacrylate, glyceryl methacrylate, 3-phenylpropyl acrylate. N,N-dimethylacrylamide, methyl methacrylate, 2-(1-naphthylethyl methacrylate) and 2-(2-naphthylethyl methacrylate).

6. The polymeric composition of claim 3 wherein said one or more hydrophobic monomers are selected from the group consisting of 2-ethylhexyl methacrylate, 3-methacryloyloxypropyldiphenylmethylsilane and 2-phenyloxyethyl methacrylate.

7. The polymeric composition of claim 4 wherein said one or more hydrophilic monomers are selected from the group consisting of N,N-dimethylacrylamide and N-methylacrylamide.

8. A polymeric composition produced through the copolymerization of one or more monomers of claim 1 with one or more aromatic or non-aromatic non-siloxy-based monomers and one or more strengthening agents.

9. A polymeric composition produced through the copolymerization of one or more monomers of claim 1 with one or more hydrophobic monomers and one or more strengthening agents.

10. A polymeric composition produced through the copolymerization of one or more monomers of claim 1 with one or more hydrophilic monomers and one or more strengthening agents.

11. A polymeric composition produced through the polymerization of one or more monomers of claim 1 with one or more strengthening agents.

12. A polymeric composition produced through the copolymerization of one or more monomers of claim 1 with one or more aromatic or non-aromatic non-siloxy-based monomers and one or more crosslinking agents.

13. A polymeric composition produced through the copolymerization of one or more monomers of claim 1 with one or more hydrophobic monomers and one or more crosslinking agents.

14. A polymeric composition produced through the copolymerization of one or more monomers of claim 1 with one or more hydrophilic monomers and one or more crosslinking agents.

15. A polymeric composition produced through the polymerization of one or more monomers of claim 1 with one or more crosslinking agents.

16. The polymeric composition of claims 8, 9, 10, 11 wherein said one or more strengthening agents are selected from the group consisting of cycloalkyl acrylates and cycloalkyl methacrylates.

17. The polymeric composition of claim 12, 13, 14 or 15 wherein said one or more crosslinking agents are selected from the group consisting of diacrylates and dimethacrylates of triethylene glycol, butylene glycol, neopentyl glycol, ethylene glycol, hexane-1,6-diol and thio-diethylene glycol, trimethylolpropane triacrylate, N,N-dihydroxyethylene bisacrylamide, diallyl phthalate, triallyl cyanurate, divinylbenzene; ethylene glycol divinyl ether, N,N'-methylene-bis-(meth)acrylamide, sulfonated divinylbenzene and divinylsulfone.

* * * * *